(12) United States Patent
Wada et al.

(10) Patent No.: US 10,208,638 B2
(45) Date of Patent: Feb. 19, 2019

(54) APPARATUS AND METHOD FOR DIAGNOSING LUBRICANT DEGRADATION IN INTERNAL COMBUSTION ENGINE

(71) Applicant: MAZDA MOTOR CORPORATION, Hiroshima (JP)

(72) Inventors: Kuniaki Wada, Hatsukaichi (JP);
Kouichi Miyamoto, Hiroshima (JP);
Kenya Ishii, Hiroshima (JP);
Tomonobu Mizuba, Hiroshima (JP);
Tomohisa Handa, Hatsukaichi (JP);
Takayoshi Fujita, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 0 days.

(21) Appl. No.: 15/397,143

(22) Filed: Jan. 3, 2017

(65) Prior Publication Data

US 2017/0198615 A1    Jul. 13, 2017

(30) Foreign Application Priority Data

Jan. 12, 2016    (JP) ................................ 2016-003287

(51) Int. Cl.
*F01M 11/10*    (2006.01)
*G01N 33/28*    (2006.01)

(52) U.S. Cl.
CPC ......... *F01M 11/10* (2013.01); *G01N 33/2835* (2013.01); *G01N 33/2888* (2013.01); *F01M 2011/1466* (2013.01); *F01M 2250/60* (2013.01); *F01M 2250/62* (2013.01)

(58) Field of Classification Search
CPC ........... G01N 33/2835; G01N 33/2888; F01M 11/10; F01M 2250/00
See application file for complete search history.

(56) References Cited

U.S. PATENT DOCUMENTS

| 5,914,890 | A | * | 6/1999 | Sarangapani | .......... F01M 11/10 702/182 |
| 6,253,601 | B1 | | 7/2001 | Wang et al. | |
| 6,513,367 | B2 | * | 2/2003 | Bondarowicz | ..... G01N 33/2888 324/672 |
| 6,920,779 | B2 | * | 7/2005 | Carlstrom | .......... G01N 33/2876 340/457.4 |
| 9,354,221 | B2 | * | 5/2016 | O'Donnell | ......... G01N 33/2888 |

(Continued)

FOREIGN PATENT DOCUMENTS

EP    1388647 A2 *  2/2004   ............. F01N 3/023
JP    H01-38250 Y2   11/1989

*Primary Examiner* — Christine A Enad
(74) *Attorney, Agent, or Firm* — Studebaker & Brackett PC

(57) ABSTRACT

An apparatus for diagnosing lubricant degradation includes a soot amount estimator configured to estimate an amount of soot formed in a predetermined period in a combustion chamber of an engine, and diagnoses the degradation of a lubricant based on a cumulative value of the amount of soot estimated. The soot amount estimator calculates the amount of soot based on a speed of the engine and a load parameter related to a load of the engine, and corrects, based on a temperature parameter correlated to the temperature of the combustion chamber, the amount of soot calculated into an increased value if the temperature parameter is lower than a predetermined first temperature.

11 Claims, 7 Drawing Sheets

(56) References Cited

U.S. PATENT DOCUMENTS

| | | | |
|---|---|---|---|
| 2003/0051696 A1* | 3/2003 | Berndorfer | F01M 11/10 123/196 R |
| 2008/0154478 A1* | 6/2008 | Lyons | F01M 1/18 701/102 |
| 2011/0166767 A1* | 7/2011 | Kurtz | F01N 9/002 701/103 |
| 2012/0090386 A1* | 4/2012 | Fischer | G01N 33/2835 73/61.71 |
| 2017/0284268 A1* | 10/2017 | Nakagawa | F01N 9/002 |

* cited by examiner

FIG. 3

| | LOW ENGINE SPEED | INTERMEDIATE ENGINE SPEED | HIGH ENGINE SPEED | |
|---|---|---|---|---|
| HIGH LOAD | $l_{11}(L)$ | $l_{12}(L)$ | $l_{13}(L)$ | ⎫ |
| INTERMEDIATE LOAD | $l_{21}(M)$ | $l_{22}(S)$ | $l_{23}(S)$ | ⎬ LOW COOLANT TEMPERATURE L |
| LOW LOAD | $l_{31}(M)$ | $l_{32}(S)$ | $l_{33}(S)$ | ⎭ |
| HIGH LOAD | $h_{11}(M)$ | $h_{12}(S)$ | $h_{13}(S)$ | ⎫ |
| INTERMEDIATE LOAD | $h_{21}(S)$ | $h_{22}(S)$ | $h_{23}(S)$ | ⎬ HIGH COOLANT TEMPERATURE H |
| LOW LOAD | $h_{31}(S)$ | $h_{32}(S)$ | $h_{33}(S)$ | ⎭ |

102 (upper), 101 (lower)

APPARATUS AND METHOD FOR DIAGNOSING LUBRICANT DEGRADATION IN INTERNAL COMBUSTION ENGINE

CROSS-REFERENCE TO RELATED APPLICATION

This application claims priority to Japanese Patent Application No. 2016-003287 filed on Jan. 12, 2016, the entire disclosure of which is incorporated by reference herein.

BACKGROUND

The present disclosure relates to an apparatus and method for diagnosing degradation of a lubricant in an internal combustion engine.

Japanese Examined Utility Model Publication No. H01-38250 describes estimation of the amount of soot formed based on the speed of an engine and the amount of fuel injected (i.e., an engine load), and diagnosis of degradation of oil based on the cumulative value of the amount of soot estimated. In this manner, the degradation of oil may be diagnosed with high accuracy based on the operational state of the engine.

SUMMARY

A study carried out by the present inventors revealed that the amount of soot formed cannot be estimated with high accuracy based on the operational state of the engine derived from the engine speed and engine load. If the temperature of a combustion chamber is low, for example, before the engine is warmed up, fuel does not vaporize easily, and the engine is instructed to inject more fuel to ensure the required amount of fuel vaporized. However, increase in the amount of fuel injected results in a longer period of time for fuel injection. Thus, the last stage of the fuel injection period overlaps with a late phase of a compression stroke, and the fuel injected during the last stage of the fuel injection period tends to turn into soot. That is, the amount of soot formed may vary depending on the temperature of the combustion chamber even if the operational state of the engine is unchanged.

In view of the foregoing, it is therefore an object of the present disclosure to diagnose degradation of a lubricant in an internal combustion engine with improved accuracy by increasing the accuracy of estimation of the amount of soot formed.

The present disclosure is directed to a method for diagnosing degradation of a lubricant in an internal combustion engine.

This method may include: estimating an amount of soot, formed in a predetermined period in a combustion chamber of the internal combustion engine, based on a speed of the internal combustion engine and a load parameter related to torque generated by the internal combustion engine; correcting the amount of soot estimated into an increased value if a temperature parameter correlated to a temperature of the combustion chamber is lower than a predetermined first temperature; calculating a cumulative value of the amount of soot estimated; and determining degradation of the lubricant in the internal combustion engine based on the cumulative value of the amount of soot.

According to this method, the instant amount of soot is estimated based on an engine speed and a parameter related to an engine load, and the amount of soot estimated is corrected based on a temperature parameter related to the temperature of the combustion chamber.

More specifically, if the temperature parameter is lower than the predetermined first temperature, the amount of soot calculated is corrected into an increased value based on the operational state of the engine. If the temperature of the combustion chamber is low, fuel does not vaporize easily, and more fuel is injected to ensure that the required amount of fuel vaporizes. The increase in the amount of fuel injected tends to cause an increase in the amount of soot formed at a low combustion chamber temperature than at a high combustion chamber temperature, even if the operational state of the engine (the engine speed and the load on the engine) remains unchanged.

The above-described method enables more accurate estimation of the amount of soot by correcting the estimated amount of soot based on a temperature parameter correlated to the temperature of the combustion chamber. In some cases, depending on the operational state of the engine, the amount of soot does not increase even if the temperature parameter is lower than the first temperature (e.g., no soot may be formed irrespective of whether the temperature of the combustion chamber is high or low). In such a case, no substantial correction may be made to the soot amount even if the temperature parameter is lower than the first temperature.

Then, the degree of degradation of a lubricant may be diagnosed more accurately when the diagnosis is made based on a cumulative value of the amount of soot estimated accurately. As a result, the user may be prompted to change the lubricant at an appropriate timing. This may reduce the risk of degradation of the engine.

If the temperature parameter is equal to or lower than a second temperature that is lower than the first temperature, estimation may be made that the amount of soot decreases as the speed of the internal combustion engine increases in a low engine speed range, and that the amount of soot increases as the speed of the internal combustion engine increases in a high engine speed range where the speed of the internal combustion engine is higher than in the low engine speed range.

In general, the gas in the combustion chamber tends to flow slowly under a low engine speed. Thus, the fuel injected in the cylinders may easily adhere to the wall surface of the combustion chamber, and an air-fuel mixture tends to be inhomogeneous. That is, the lower the engine speed is, the more easily the soot is formed. Stated otherwise, an increase in engine speed results in a decrease in the amount of soot formed.

Therefore, if the temperature parameter is equal to or lower than the second temperature in a low engine speed range where the engine speed is relatively low, the amount of soot is estimated such that the amount of soot decreases as the engine speed increases. Thus, the amount of soot may be estimated with improved accuracy.

In a high engine speed range where the engine speed is relatively high, it takes a shorter time for the crank angle to change by one degree. As described above, if the temperature parameter is equal to or lower than the second temperature, i.e., if the temperature of the combustion chamber is low, fuel does not vaporize easily, and a larger amount of fuel is injected. Thus, it takes a longer time for fuel injection (i.e., the actual amount of time taken for the injection increases). If the temperature parameter is equal to or lower than the second temperature and the engine speed increases in the high engine speed range where the engine speed is high, fuel injected during the last stage of the injection period may easily adhere to the wall surface of the combustion chamber, thus resulting in an increase in the amount of soot formed.

In view of the foregoing, if the temperature parameter is equal to or lower than the second temperature in the high engine speed range, estimation is made that the amount of soot increases as the engine speed increases. Thus, the amount of soot may be estimated with improved accuracy.

If the temperature parameter is higher than the second temperature and lower than the first temperature, the rate of increase in the amount of soot with the increase in speed of the internal combustion engine may be allowed to decrease in the high engine speed range as the temperature parameter increases.

As described above, a larger amount of fuel is injected if the temperature parameter is low. Thus, in the high engine speed range, the amount of soot increases as the engine speed increases. On the other hand, if the temperature parameter increases, the amount of fuel injected decreases accordingly, and the soot is formed less easily. That is, in the high engine speed range, the rate of increase in the amount of soot with the increase in the engine speed decreases as the temperature parameter increases. The rate of increase in the amount of soot may be defined as the gradient of a two-dimensional graph, of which the abscissa represents the engine speed and the ordinate represents the amount of soot.

Therefore, if the temperature parameter is higher than the second temperature and lower than the first temperature, the rate of increase in the amount of soot with the increase in the engine speed is allowed to decrease in the high engine speed range as the temperature parameter increases. Thus, the amount of soot may be estimated with improved accuracy.

In the above-described method, the amount of soot may be estimated based on the speed of the internal combustion engine, the load parameter, and first temperature data if the temperature parameter is equal to or higher than the first temperature, and may be estimated based on the speed of the internal combustion engine, the load parameter, and second temperature data if the temperature parameter is equal to or lower than the second temperature, the first temperature data representing a relationship among the speed of the internal combustion engine, the load parameter, and the amount of soot when the temperature parameter is the first temperature, the second temperature data representing a relationship among the speed of the internal combustion engine, the load parameter, and the amount of soot when the temperature parameter is the second temperature. If the temperature parameter is higher than the second temperature and lower than the first temperature, a first temperature soot amount may be calculated based on the speed of the internal combustion engine, the load parameter, and the first temperature data, a second temperature soot amount may be calculated based on the speed of the internal combustion engine, the load parameter, and the second temperature data, and the amount of soot may be estimated by linear interpolation between the first and second temperature soot amounts. The first and second temperature data may be collected from an actual engine.

According to the above-described configuration, if the temperature parameter is equal to or higher than the first temperature, i.e., if the temperature of the combustion chamber is higher than the predetermined value, the amount of soot formed does not change significantly even if the temperature varies. Thus, the amount of soot is estimated based on the engine speed, the load parameter, and the first temperature data. That is to say, the amount of soot is estimated based on the operational state of the engine and the first temperature data, and does not change even if the temperature varies. Thus, the amount of soot may be estimated with high accuracy. In this context, the amount of soot estimated may sometimes be equal to zero.

If the temperature parameter is equal to or lower than the second temperature, i.e., if the temperature of the combustion chamber is lower than the predetermined value, the amount of soot is estimated based on the engine speed, the load parameter, and the second temperature data. That is to say, the amount of soot is estimated based on the operational state of the engine and the second temperature data.

If the temperature parameter is higher than the second temperature and lower than the first temperature, both of the first and second temperature data are used. Specifically, the first temperature soot amount is calculated based on the engine speed, the load parameter, and the first temperature data. In addition, the second temperature soot amount is calculated based on the engine speed, the load parameter, and the second temperature data. Then, the amount of soot at the current temperature parameter is estimated by linear interpolation between the first and second temperature soot amounts. In this way, the amount of soot may be estimated with improved accuracy, while the amount of data to be stored is reduced as much as possible.

Disclosed herein is an apparatus for diagnosing degradation of a lubricant in an internal combustion engine.

The apparatus may include: a first sensor configured to detect a speed of the internal combustion engine and output a detection signal; a second sensor configured to detect a load parameter related to torque generated by the internal combustion engine and output a detection signal; a third sensor configured to detect a temperature parameter correlated to a temperature of a combustion chamber and output a detection signal; a soot amount estimator configured to receive the detection signals from the first, second, and third sensors, and calculate an amount of soot formed in a predetermined period in the combustion chamber of the internal combustion engine based on the speed of the internal combustion engine and the load parameter; and a diagnostic unit configured to diagnose degradation of the lubricant based on a cumulative value of the amount of soot estimated by the soot amount estimator. The soot amount estimator may correct, based on the temperature parameter, the amount of soot calculated into an increased value when determining the temperature parameter to be lower than a predetermined first temperature.

When determining the temperature parameter to be equal to or lower than a second temperature that is lower than the first temperature, the soot amount estimator may estimate that the amount of soot decreases as the speed of the internal combustion engine increases in a low engine speed range, and that the amount of soot increases as the speed of the internal combustion engine increases in a high engine speed range where the speed of the internal combustion engine is higher than in the low engine speed range.

When determining the temperature parameter to be higher than the second temperature and lower than the first temperature, the soot amount estimator may allow the rate of increase in the amount of soot with the increase in the speed of the internal combustion engine to decrease in the high engine speed range as the temperature parameter increases.

The soot amount estimator may store first temperature data representing a relationship among the speed of the internal combustion engine, the load parameter, and the amount of soot when the temperature parameter is the first temperature, and second temperature data representing a relationship among the speed of the internal combustion engine, the load parameter, and the amount of soot when the temperature parameter is the second temperature. The soot amount estimator may estimate the amount of soot based on the speed of the internal combustion engine, the load parameter, and the first temperature data when determining the temperature parameter to be equal to or higher than the first temperature, and may estimate the amount of soot based on the speed of the internal combustion engine, the load parameter, and the second temperature data when determining the temperature parameter to be equal to or lower than the second temperature. Further, when determining the temperature parameter to be higher than the second temperature and lower than the first temperature, the soot amount estimator may calculate a first temperature soot amount based on the speed of the internal combustion engine, the load parameter, and the first temperature data, may calculate a second temperature soot amount based on the speed of the internal combustion engine, the load parameter, and the second temperature data, and may estimate the amount of soot by linear interpolation between the first and second temperature soot amounts.

BRIEF DESCRIPTION OF THE DRAWINGS

FIG. 3 is a conceptual diagram illustrating a first temperature data map and a second temperature data map used for soot amount estimation.

DETAILED DESCRIPTION

Figure 1:
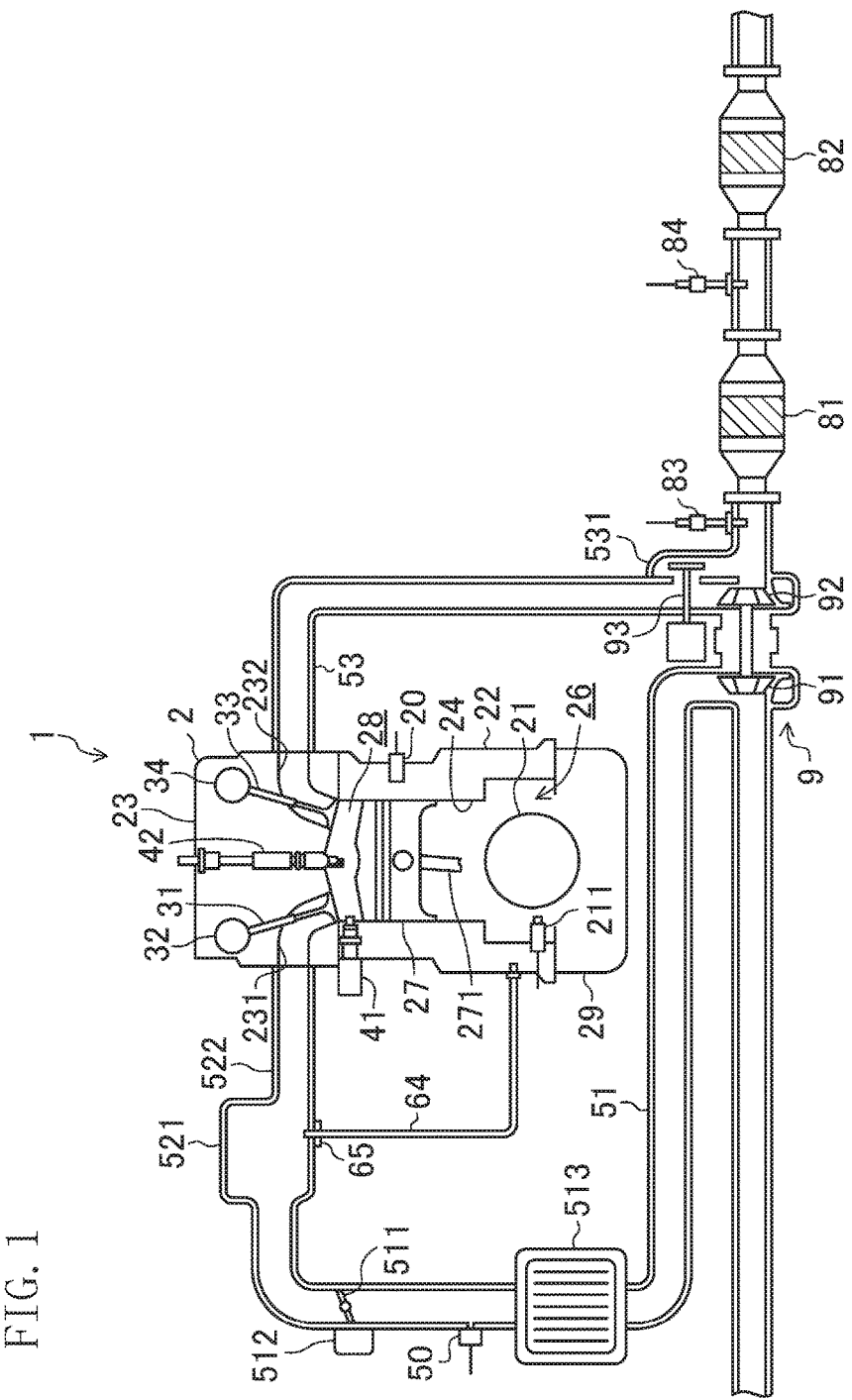
FIG. 1 is a conceptual diagram illustrating an engine system to which an apparatus for diagnosing degradation of a lubricant in an internal combustion engine is applied.
Figure 7:
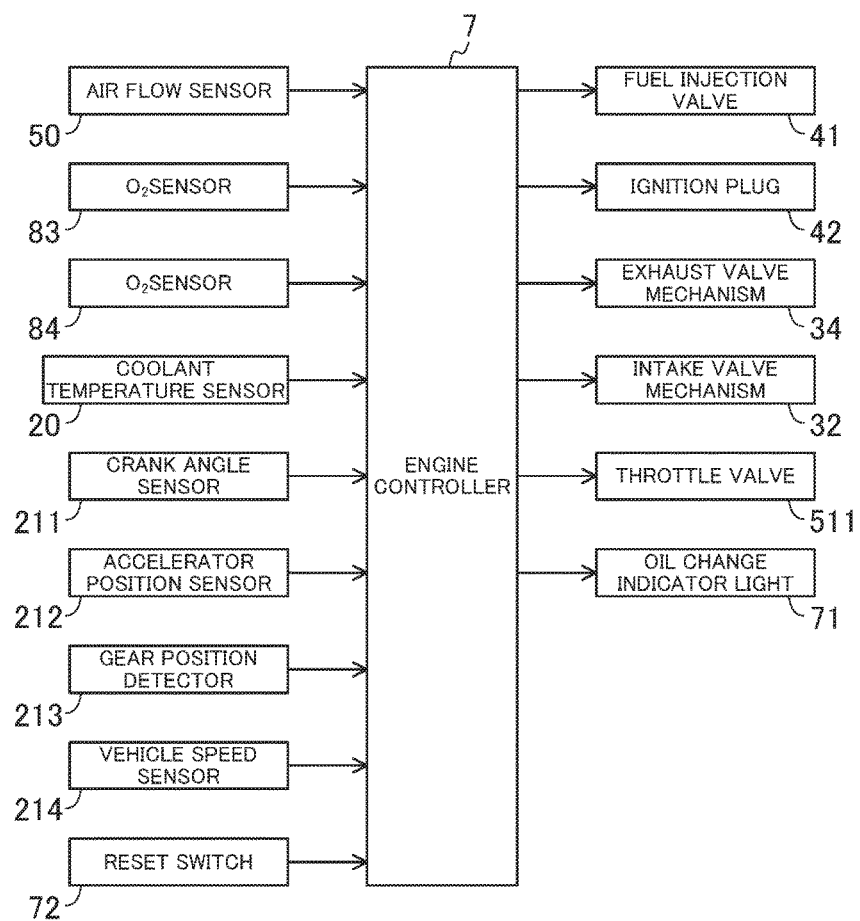
FIG. 7 is a block diagram illustrating a configuration for an engine system.

An apparatus for diagnosing degradation of a lubricant in an internal combustion engine will be described below with reference to the drawings. Described below is an exemplary embodiment of an apparatus for diagnosing degradation of a lubricant in an internal combustion engine. FIG. 1 illustrates an engine system 1 to which a lubricant degradation diagnostic apparatus 10 (see FIG. 2) is applied. FIG. 7 is a block diagram illustrating a configuration for the engine system 1.

The engine system 1 includes an engine 2 configured as a spark ignition internal combustion engine. The engine 2 is a turbocharged engine. Though not shown, the engine 2 is mounted horizontally in an engine room at a frontend of a vehicle such as an automobile. Alternatively, the engine 2 may also be vertically mounted. A crankshaft 21 as an output shaft of the engine 2 is coupled to driving wheels via a transmission (not shown). The output of the engine 2 transmitted to the driving wheels allows a vehicle to travel.

The engine 2 includes a cylinder block 22, and a cylinder head 23 mounted on the cylinder block 22. The cylinder block 22 houses a plurality of cylinders 24. In this exemplary embodiment, the engine 2 includes four cylinders 24. The four cylinders 24 are arranged in the direction coming out of the paper of FIG. 1. The number and arrangement of the cylinders 24 in the engine 2 are not particularly limited.

An oil pan 29 configured to store a lubricant is attached to the bottom of the cylinder block 22. The cylinder block 22 defines a crankcase 26 housing the crankshaft 21. The engine 2 includes a crank angle sensor 211 which detects the speed of the crankshaft 21, i.e., the speed of the engine 2.

The crankshaft 21 is coupled to a piston 27 via a connecting rod 271, which is shown only partially in FIG. 1. The piston 27 is inserted reciprocatably in each of the cylinders 24. The piston 27, the cylinder head 23, and the cylinders 24 define a combustion chamber 28.

The cylinder head 23 includes intake ports 231, each being provided for an associated one of the cylinders 24. The intake ports 231 communicate with the combustion chamber 28. An intake valve 31 is arranged in each of the intake ports 231 to selectively block the intake port 231 from the combustion chamber 28. The intake valves 31 are driven by an intake valve mechanism 32. Each of the intake valves 31 opens or closes the associated intake port 231 at a predetermined timing.

The cylinder head 23 also includes exhaust ports 232, each being provided for an associated one of the cylinders 24. The exhaust ports 232 communicate with the combustion chamber 28. An exhaust valve 33 is arranged in each of the exhaust ports 232 to selectively block the exhaust port 232 from the combustion chamber 28. The exhaust valves 33 are driven by an exhaust valve mechanism 34. Each of the exhaust valves 33 opens or closes the associated exhaust port 232 at a predetermined timing.

The intake valve mechanism 32 and the exhaust valve mechanism 34 have an intake camshaft and an exhaust camshaft, respectively (not shown). These camshafts are coupled to, and driven by, the crankshaft 21 via a timing chain (not shown). The intake camshaft and the exhaust camshaft rotate as the crankshaft 21 rotates.

The intake valve mechanism 32 is configured to be ready to change the lift and opening period of the intake valves 31. Any of various known configurations may be adopted for the intake valve mechanism 32. The intake valve mechanism 32 may be configured to continuously change the lift and opening period of the intake valves 31 using an oil pressure raised by the camshaft, for example. Although not shown, the intake valve mechanism 32 changes the lift and opening period of the intake valves 31 in response to a signal from an engine controller 7.

The exhaust valve mechanism 34 is also configured to be ready to change the lift and opening period of the exhaust valves 33. Any of various known configurations may be adopted for the exhaust valve mechanism 34. The exhaust valve mechanism 34 may be configured to continuously change the lift and opening period of the exhaust valves 33 using an oil pressure raised by the camshaft, for example. Although not shown, the exhaust valve mechanism 34 changes the lift and opening period of the exhaust valves 33 in response to a signal from the engine controller 7.

The intake ports 231 are connected to an intake passage 51. The intake passage 51 introduces intake air to the cylinders 24. A throttle valve 511 is arranged halfway through the intake passage 51. The throttle valve 511 is an electrically controlled valve. A throttle actuator 512 adjusts the degree of opening of the throttle valve 511 in response to a control signal from the engine controller 7.

A compressor 91 of a turbocharger 9 is arranged upstream of the throttle valve 511 in the intake passage 51. Intake air is supercharged when the compressor 91 is operated. An intercooler 513 is arranged between the throttle valve 511 and the compressor 91 to cool the air compressed by the compressor 91.

A surge tank 521 and an independent passage 522 are arranged downstream of the throttle valve 511 in the intake passage 51. The independent passage 522 is ramified into the four cylinders 24 downstream of the surge tank 521.

An air flow sensor 50 is arranged downstream of the compressor 91 in the intake passage 51. The air flow sensor 50 senses the amount and temperature of the intake air introduced into the cylinders 24.

An exhaust passage 53 is connected to the exhaust ports 232. The exhaust passage 53 is equipped with a turbine 92 of the turbocharger 9. An exhaust gas flow rotates the turbine 92, which in turn activates the compressor 91 coupled to the turbine 92.

The exhaust passage 53 is also connected to an exhaust bypass passage 531 that bypasses the exhaust gas via the turbine 92. The exhaust bypass passage 531 is equipped with a wastegate valve 93. The wastegate valve 93 regulates the flow rate of the exhaust gas flowing through the exhaust bypass passage 531. The larger the degree of opening of the wastegate valve 93 is, the higher the flow rate of the exhaust gas flowing through the exhaust bypass passage 531 becomes, and the lower the flow rate of the exhaust gas flowing toward the turbine 92 becomes.

A first catalytic device 81 and a second catalytic device 82 are arranged downstream of the turbine 92 in the exhaust passage 53. The first and second catalytic devices 81 and 82 are configured to purify the exhaust gas. The exhaust passage 53 is further provided with two $O_2$ sensors 83 and 84 to detect the oxygen concentration in the exhaust gas. Each of the $O_2$ sensors 83 and 84 sends a detection signal to the engine controller 7.

The cylinder head 23 further includes fuel injection valves 41 respectively associated with the cylinders 24. The fuel injection valves 41 are configured to inject a fuel (e.g., gasoline or a fuel containing gasoline) directly into the cylinders 24. The fuel injection valves 41 may be of any type, but may be configured as multi-port injection valves, for example. The fuel injection valves 41 inject a predetermined amount of fuel into the cylinders 24 at a predetermined timing in response to a fuel injection pulse from the engine controller 7. In the example shown in FIG. 1, the fuel injection valves 41 are attached to the intake side of the cylinders 24. However, this is only an example, and the fuel injection valves 4 may alternatively be attached to the other side of the cylinders 24 as well.

The cylinder head 23 further includes ignition plugs 42 respectively associated with the cylinders 24. Each of the ignition plugs 42 has an electrode located on the shaft center of an associated one of the cylinders 24 on a ceiling of the cylinder head 23. The ignition plugs 42 generate a spark in the combustion chamber 28 to ignite an air-fuel mixture in the combustion chamber 28. The ignition plugs 42 generate a spark at a desired ignition timing in accordance with an ignition signal from the engine controller 7.

The engine 2 further includes a communicating path 64 configured to allow a blowby gas leaked from the combustion chamber 28 to flow back into the intake passage 51. The communicating path 64 is implemented as a hose which allows the crankcase 26 of the engine 2 to communicate with the surge tank 521. The communicating path 64 passes the blowby gas in the crankcase 26 into the surge tank 521. The surge tank 521 is provided with a PCV (Positive Crankcase Ventilation) valve 65. The communicating path 64 is connected to the PCV valve 65 which regulates the flow rate of the blowby gas in the communicating path 64. In this exemplary embodiment, the PCV valve 65 is configured as a mechanical valve which adjusts the degree of opening in accordance with a pressure difference between the crankcase 26 and the intake passage 51. Note that the PCV valve 65 is not always provided for the surge tank 521, but may alternatively be attached to an oil separator (not shown) on the side surface of the cylinder block 22 of the engine 2.

A coolant temperature sensor 20 is attached to a coolant passage of the engine 2 to detect the temperature of a coolant. As will be described later, the engine controller 7 is connected to an oil change indicator light 71 which is lit to prompt the user to change the lubricant, and is also connected to a reset switch 72 which will be operated when the lubricant has been changed. The reset switch does not have to be a hardware switch, but may also be configured as a software switch of a touchscreen panel that displays various interactive images on the screen.

The engine system 1 includes a degradation diagnostic apparatus 10 which diagnoses the degree of lubricant degradation. Based on the diagnosis made by the degradation diagnostic apparatus 10, the engine system 1 alerts the user to change the lubricant. The lubricant degradation is diagnosed and the user is prompted to change the lubricant in order to reduce the possible wear of a timing chain. More specifically, increase in the amount of soot in the lubricant for lubricating the chain accelerates the wear of the timing chain, thus resulting in a decline in the performance of the engine. Thus, the degree of lubricant degradation is diagnosed to prompt the user to change the lubricant at an appropriate timing based on the diagnosis. Replacement of an old lubricant with a new one in response to the alert may retard the wear of the timing chain and reduce a decline in the engine performance. The engine system 1 may include an electronically controlled valve as the PCV valve 65 to ventilate the crankcase 26 at an appropriate timing by allowing the engine controller 7 to increase, if necessary, the opening of the PCV valve 65 based on the operational state of the engine 2, irrespective of the pressure difference between the crankcase 26 and the intake passage 51. This configuration may also reduce the risk of contamination of the lubricant with the fuel and the soot.

Figure 2:
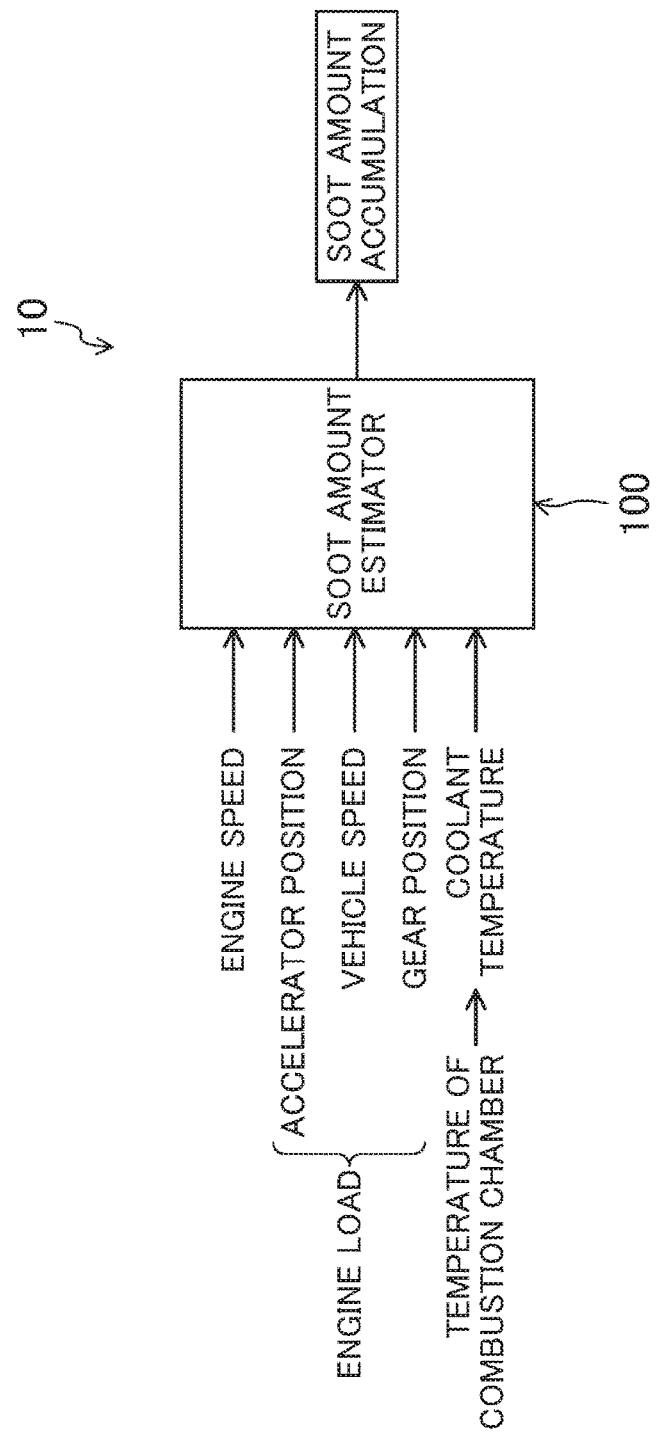
FIG. 2 is a block diagram illustrating a configuration for a soot amount estimator of the apparatus for diagnosing degradation of a lubricant in an internal combustion engine.

FIG. 2 shows a configuration for a soot amount estimator 100 of the lubricant degradation diagnostic apparatus 10. The soot amount estimator 100 is implemented as an engine controller 7. The engine controller 7 is a controller, the functions of which are basically performed by a well-known microcomputer. The engine controller 7 includes a central processing unit (CPU) which executes programs, a memory configured as, for example, a random access memory (RAM) or a read only memory (ROM), for storing programs and data, and an input/output bus which inputs and outputs an electrical signal.

The soot amount estimator 100 estimates the amount of soot formed in a predetermined period (of, e.g., 0.1 sec) in the combustion chamber 28 of the engine 2. The lubricant degradation diagnostic apparatus 10 calculates a cumulative value of the amount of soot estimated, and lights the oil change indicator light 71 when the cumulative amount of soot reaches a predetermined amount.

The soot amount estimator 100 estimates the amount of soot based on the engine speed, the engine load, and the temperature of the combustion chamber 28. The engine speed is detected based on a detection signal from the crank angle sensor 211. In this example, the engine load is determined based on the values detected by an accelerator position sensor 212, a vehicle speed sensor 214, and a gear position detector 213. Note that the engine load may be estimated based on the values detected by the air flow sensor 50, i.e., the amount and temperature of the air introduced into the cylinders 24. Alternatively, the engine load may be estimated based on the amount of fuel injected, for example.

In this example, the temperature of the combustion chamber is estimated based on the temperature of a coolant in the engine 2, i.e., the detection signal of the coolant temperature sensor 20. The temperature of the coolant is proportional to the temperature of the combustion chamber. The temperature of the combustion chamber may alternatively be estimated based on the temperature of the lubricant or exhaust gas correlated to the temperature of the combustion chamber, instead of the temperature of the coolant. Still alternatively, the temperature of the combustion chamber 28 may be directly detected.

The soot amount estimator 100 stores two temperature data maps. FIG. 3 conceptually shows the two temperature data maps. The temperature data maps are comprised of a first temperature data map 101 at a high coolant temperature H (i.e., at a first temperature parameter of 90° C., for example), and a second temperature data map 102 at a low coolant temperature L (i.e., at a second temperature parameter of 20° C., for example). Each of the data maps 101 and 102 may be created based on data collected from an actual engine or through a simulation.

In the example shown in FIG. 3, each of the data maps 101 and 102 is a matrix of rows indicating the engine speed and columns indicating the engine load. Each of the data maps 101 and 102 indicates the amount of soot ($1_{ij}$ and $h_{ij}$, where i=1 to 3 and j=1 to 3) which may be formed in the combustion chamber 28 with respect to various operational states of the engine represented by the engine speed and the load on the engine. Each of the data maps 101 and 102 classifies the engine speeds into three ranges, namely, low, intermediate, and high, and the engine loads into three ranges, namely, low, intermediate, and high. The speeds of the engine 2 are not necessarily classified into three ranges as shown in FIG. 3, but may be classified into two, or four or more ranges. Likewise, the loads on the engine 2 are not necessarily classified into three ranges as shown in FIG. 3, but may be classified into two, or four or more ranges.

Next, it will be described with reference to FIGS. 3 and 4 how the soot amount tends to change as the operational state of the engine 2 varies. In the first and second temperature data maps 101 and 102 shown in FIG. 3, "L," "M," and "S" indicate that the soot amount ($1_{ij}$ and $h_{ij}$) is large, medium, or small, respectively. The sign "S" also encompasses a situation where the soot amount is equal to zero.

First, it will be described how much soot tends to be formed when the coolant temperature is high in the first temperature data map 101. If the coolant temperature is high and the engine load is low or intermediate, the amount of soot formed is small irrespective of the engine speed. Under a high engine load (i.e., if a gas load of this turbocharged engine is 1.0 or more), the soot amount is medium if the engine speed is low, but the soot amount is small if the engine speed is high. If the engine load is high, more fuel is injected, and thus the soot is formed more easily than under a low or intermediate engine load. If the engine speed is low, the gas in the combustion chamber 28 tends to flow more slowly. Thus, the fuel comes to adhere more easily to the wall surface of the combustion chamber 28, and an air-fuel mixture is prone to be inhomogeneous. Meanwhile, if the engine speed is high, the gas in the combustion chamber 28 tends to flow faster, and the fuel comes to rarely adhere to the wall surface of the combustion chamber 28. On the other hand, if the coolant temperature and the engine speed are both high, the temperature at the wall surface of the combustion chamber 28 rises, which facilitates vaporization of the fuel, even if the fuel has adhered to the wall surface of the combustion chamber 28. Further, the air-fuel mixture is prone to be homogeneous because the gas flows rather fast in the combustion chamber. Thus, the lower the engine speed is, the more likely the soot amount increases as shown in FIG. 4, if the coolant temperature and the engine load are both high. The values $h_{11}$, $h_{12}$, and $h_{13}$ shown in FIG. 4 correspond respectively to the values $h_{11}$, $h_{12}$, and $h_{13}$ shown in FIG. 3. However, the amount of soot formed under the high coolant temperature condition is less than that under the low coolant temperature condition.

Next, it will be described how much soot tends to be formed when the coolant temperature is low in the second temperature data map 102. The amount of soot formed under the low coolant temperature condition is larger than that formed under the high coolant temperature condition. This is because the low coolant temperature leads to a lower temperature in the combustion chamber, thus preventing the fuel from vaporizing easily. In addition, the decrease in the vaporization of the fuel requires correcting the amount of fuel injected into an increase value compared to a situation where the engine is operated at the high coolant temperature and the same engine load so that the required amount of vaporized fuel is ensured to achieve the engine load estimated or determined by the engine controller 7. The increase in the amount of fuel injected causes an increase in the amount of time taken for the fuel injection valves 41 to inject the fuel for a single combustion, and the fuel injected during the last stage of the injection period comes to adhere to the wall surface of the combustion chamber 28 more easily. The low coolant temperature leads to a lower temperature at the wall surface of the combustion chamber 28, which prevents the fuel adhered to the wall surface from vaporizing easily. Therefore, more soot is formed than under the high coolant temperature condition.

Even if the coolant temperature is low, low or intermediate engine load results in a decrease in the soot amount formed, compared to a situation where the engine load is high. Further, even under the low coolant temperature condition, the same tendency is observed as in a situation where the coolant temperature is high, i.e., the soot amount is "medium" under the low engine speed, and is "low" under the high engine speed, if the engine load is low.

On the other hand, if the coolant temperature is low and the engine load is intermediate or high, the soot formation shows a different tendency relative to the engine speed from that observed under the high coolant temperature condition. Specifically, as shown in FIG. 4, the soot amount decreases as the engine speed increases in a low engine speed range where the engine speed is relatively low (i.e., in a left half range of the graph shown in FIG. 4). The values $1_{11}$, $1_{12}$, and $1_{13}$ shown in FIG. 4 respectively correspond to the values $1_{11}$, $1_{12}$, and $1_{13}$ shown in FIG. 3. As described above, the higher the engine speed is, the faster the gas tends to flow in the combustion chamber 28. Thus, the fuel comes to adhere to the wall surface of the combustion chamber 28 less easily. In addition, the faster gas flow easily makes the air-fuel mixture homogenous.

In contrast, in a high engine speed range where the engine speed is relatively high under the low coolant temperature condition (i.e., in a right half range of the graph shown in FIG. 4), the soot amount increases as the engine speed increases. This is because the low coolant temperature and the relatively high load on the engine 2 significantly increase the amount of fuel injected, thus extending the fuel injection period (i.e., the actual amount of time taken for the injection). In addition, the increase in the speed of the engine 2 leads to a decrease in the actual amount of time taken for the crank angle to change by one degree, the last stage of the injection time overlaps with a late phase of a compression stroke (e.g., a latter half of the compression stroke), and the fuel injected during the last stage comes to adhere to the wall surface of the combustion chamber 28 more easily. If the coolant temperature is high, the temperature of the combustion chamber is also high, which allows the fuel, even if adhered to the wall surface of the combustion chamber 28, to vaporize easily. However, under the low coolant temperature, the fuel adhered to the wall surface does not vaporize easily, which leads to easy soot formation.

Figure 4:
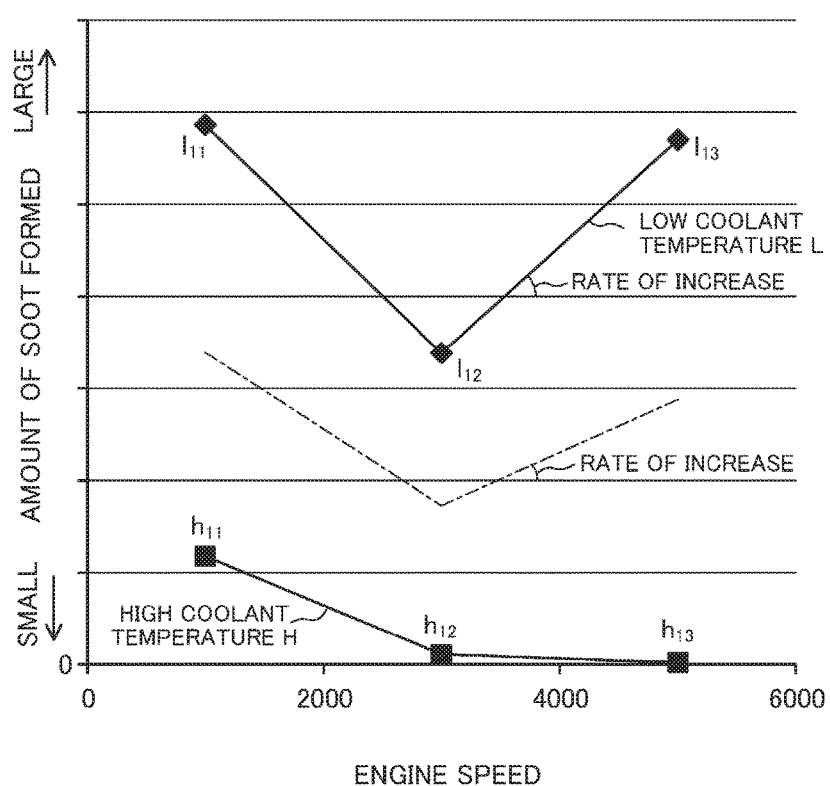
FIG. 4 is a graph illustrating exemplary relationships between an engine speed and an amount of soot formed in a high load range.

Thus, if the coolant temperature is low and the engine load is intermediate or high, the soot formation shows a different tendency as shown in FIG. 4 relative to the speed of the engine 2 from the one observed under the high coolant temperature condition.

The soot amount estimator 100 estimates the soot amount based on the engine speed and the engine load using the first temperature data map 101 if the coolant temperature is equal to or higher than the high coolant temperature H. That is, the value (h) on the first temperature data map 101 is estimated as it is as the soot amount. On the other hand, the soot amount estimator 100 estimates the soot amount based on the engine speed and the engine load using the second temperature data map 102 if the coolant temperature is equal to or lower than the low coolant temperature L. That is, the value ($1_{ij}$) on the first temperature data map 101 is estimated as it is as the soot amount.

Figure 5:
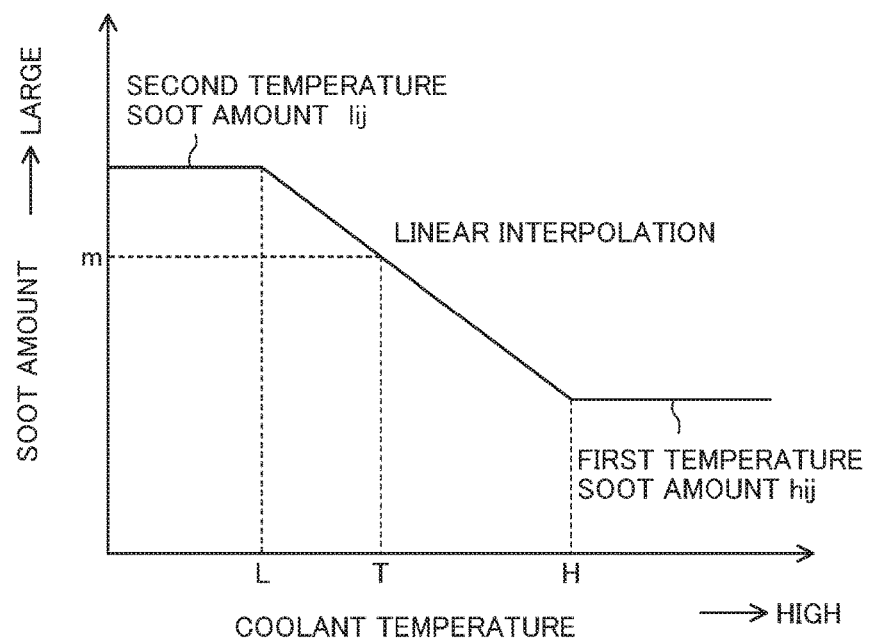
FIG. 5 is a graph illustrating a relationship between a coolant temperature and an amount of soot estimated under a predetermined operational state of the engine.

The soot amount estimator 100 estimates the soot amount using both of the first and second temperature data maps 101 and 102 if the coolant temperature is higher than the low coolant temperature (L) and lower than the high coolant temperature (H), e.g., if the coolant temperature is T (see FIG. 5). Specifically, the soot amount estimator 100 calculates, based on the engine speed and the load on the engine, a first temperature soot amount ($h_{ij}$) by reference to the first temperature data map 101, and a second temperature soot amount ($1_{ij}$) by reference to the second temperature data map 102. Then, as shown in FIG. 5, the soot amount at the coolant temperature T is estimated by linear interpolation between the first and second temperature soot amounts $h_{ij}$ and $1_{ij}$.

Thus, the linear interpolation performed if the coolant temperature is higher than the low coolant temperature L and lower than the high coolant temperature H allows the rate of increase in the soot amount (i.e., the gradient of the two-dimensional graph of FIG. 4) with the variation in the engine speed to decrease as the coolant temperature increases in the high engine speed range under the high engine load as indicated by the one-dot chain in FIG. 4.

As described above, if the coolant temperature is high (H) in the high engine speed range under the high load, the soot amount is smaller than that in the low engine speed range. In contrast, if the coolant temperature is low (L) in the high engine speed range under the high load, the fuel injection period increases as the engine speed increases, and thus the speed of a piston also increases, thereby allowing the fuel injected during the last stage of the injection period to adhere more easily to the wall surface of the combustion chamber and the surface of a piston crown. In addition, the fuel injected is not allowed to vaporize easily in such an environment, and thus more soot is formed than in the low engine speed range. Once the temperature of the combustion chamber 28 is raised, the fuel injected in the combustion chamber 28 comes to vaporize easily, and the rate of increase in the amount of fuel injection required to achieve the same engine load decreases as compared with a situation where the coolant temperature is high. Thus, the soot amount decreases. As a result, if the coolant temperature increases, the rate of increase in the soot amount with the variation in the engine speed decreases.

In this way, the soot amount estimator 100 estimates the amount of soot formed in a predetermined period based on the engine speed, engine load, and coolant temperature at a given point in time.

Figure 6:
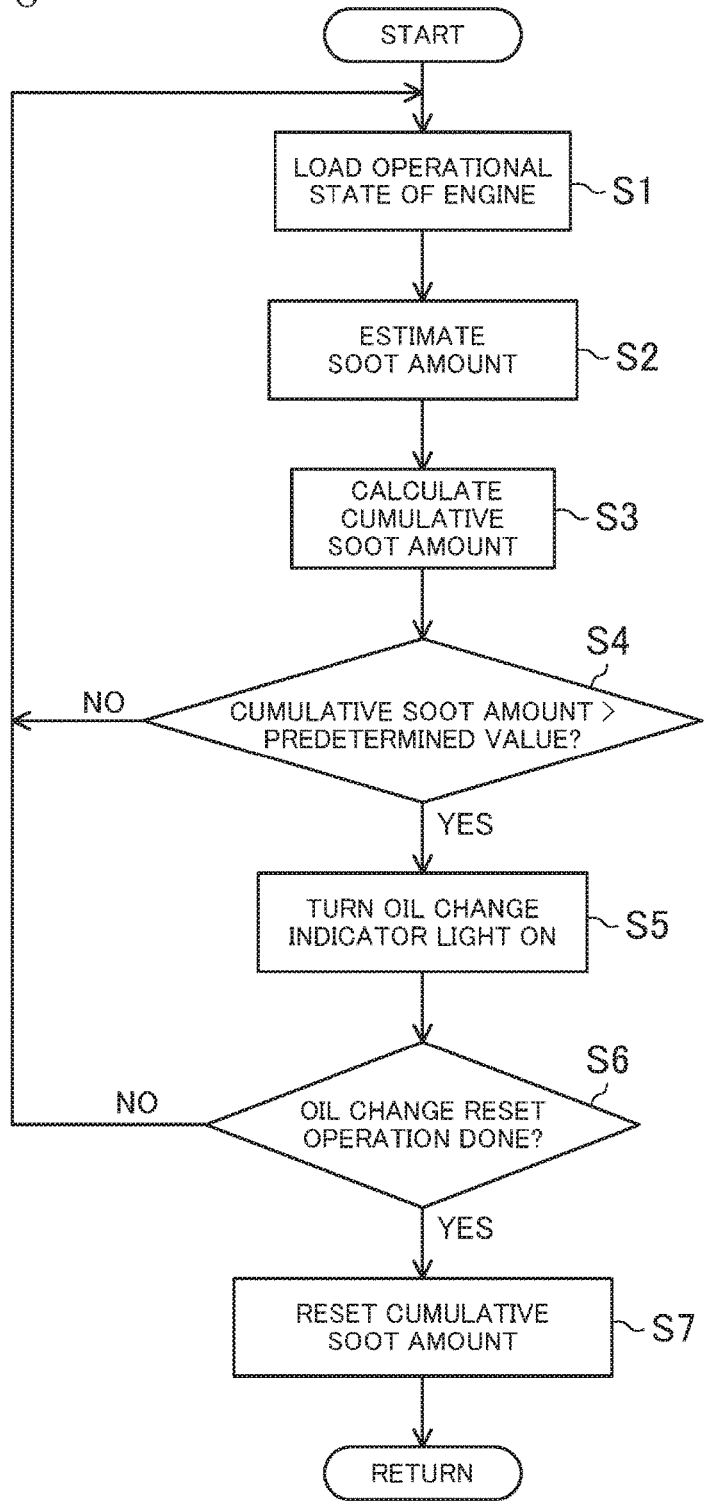
FIG. 6 is a flowchart showing an exemplary procedure for a diagnosis of lubricant degradation.

FIG. 6 is a flowchart showing a procedure in which a diagnosis of lubricant degradation is made by the degradation diagnostic apparatus 10. This flow starts when the engine 2 is activated, and ends when the engine 2 is stopped. This flow is repeated at regular intervals while the engine 2 is operating.

First, in Step S1, the operational state of the engine 2 is loaded. More specifically, as shown in FIG. 2, the engine speed, the position of an accelerator, the vehicle speed, the gear position, and the coolant temperature are loaded.

In the next Step S2, as described above, the first temperature data map 101 and/or the second temperature data map 102 are/is used depending on the coolant temperature to estimate the amount of soot formed in a predetermined period according to the operational state of the engine 2. A cumulative value of the amount of soot estimated is calculated in Step S3, and a determination is made in Step S4 whether or not the cumulative amount of soot has exceeded a predetermined value. If the answer to the question of Step S4 is NO, the process goes back to Step S1 to repeat the estimation of the amount of soot formed in the predetermined period and the accumulation of the estimated amount of soot.

On the other hand, if the answer to the question of Step S4 is YES, the process proceeds to Step S5 to turn ON the oil change indicator light 71 so that the user is prompted to change the lubricant.

In Step S6, a determination is made whether or not a reset operation has been performed after the lubricant has been changed, i.e., whether or not the reset switch 72 has been turned ON. In the absence of the reset operation, the process goes back from Step S6 to Step S1 to repeat the estimation of the soot amount and the accumulation of the estimated soot amount. Since the cumulative soot amount remains above the predetermined value, the oil change indicator light 71 is kept lit in Step S5.

Once the reset operation is done, the process proceeds from Step S6 to Step S7 to reset the cumulative soot amount, and then the process returns to Step S1. In this case, since the cumulative soot amount becomes zero, the answer to the question of Step S4 becomes NO, and thus the oil change indicator light 71 is turned OFF.

As can be seen from the foregoing, the lubricant degradation diagnostic apparatus 10 disclosed herein includes the soot amount estimator 100 configured to estimate the amount of soot formed in a predetermined period in the combustion chamber 28 of the engine 2, and diagnose the degradation of the lubricant based on a cumulative value of the amount of soot estimated.

Using the first temperature data map 101 and/or the second temperature data map 102, the soot amount estimator 100 calculates the soot amount based on the speed of the engine 2 and load parameters related to the load on the engine 2 (the amount and temperature of the intake air in this example). Further, the soot amount estimator 100 corrects the soot amount calculated into an increased value based on a temperature parameter correlated to the temperature of the combustion chamber 28 (e.g., the coolant temperature proportional to the temperature of the combustion chamber 28 in this example) if the temperature parameter is lower than a predetermined first temperature (i.e., the high coolant temperature H) (see FIG. 5).

More particularly, if the coolant temperature is lower than the high coolant temperature H, the soot amount is estimated by linear interpolation using the first and second temperature data maps 101 and 102, or by using the second temperature data map 102 only. The soot amount thus estimated becomes larger than the soot amount ($h_{ij}$) on the first temperature data map 101.

If the temperature of the combustion chamber 28 is low, the fuel does not vaporize easily, and more fuel is injected to ensure the required amount of the fuel vaporized. Thus, the soot amount tends to increase.

According to the above-described configuration, the soot amount calculated is corrected based on the coolant temperature proportional to the temperature of the combustion chamber 28. Thus, the soot amount may be estimated with improved accuracy.

In some cases, depending on the operational state of the engine 2, the soot amount does not increase even if the coolant temperature is lower than the high coolant temperature H (e.g., as shown in FIG. 3, if the engine load is low and the engine speed is intermediate or high, the soot amount is small irrespective of whether the coolant temperature is high or low). In such a case, a correction to increase the soot amount estimated based on the coolant temperature compared to the value on the first temperature data, that is, linear interpolation based on the first and second temperature data, is not substantially performed.

Then, based on the cumulative value of the amount of soot estimated with high accuracy, the degree of lubricant degradation may be diagnosed with improved accuracy. As a result, the user may be prompted to change the lubricant at an appropriate timing. This may reduce the risk of degradation of the engine 2.

If the coolant temperature is equal to or lower than the second temperature (i.e., the low coolant temperature L), the soot amount estimator 100 makes estimation that the soot amount decreases as the speed of the engine 2 increases in the low engine speed range, and makes estimation that the soot amount increases as the speed of the engine 2 increases in the high engine speed range where the engine speed is higher than in the low engine speed range (see FIG. 4).

In general, when the speed of the engine 2 is low, the gas in the combustion chamber 28 tends to flow more slowly. Thus, the fuel injected in the cylinders 24 comes to adhere to the wall surface of the combustion chamber 28 more easily, and the air-fuel mixture tends to be inhomogeneous. Therefore, the lower the engine speed is, the more easily the soot is formed. As the engine speed increases, the piston speed also increases, and the gas starts flowing faster. Thus, the soot amount tends to decrease compared to a situation where the engine speed is relatively low.

Thus, as shown in FIG. 4, if the coolant temperature is equal to or lower than the low coolant temperature L in the low engine speed range where the speed of the engine 2 is relatively low, estimation is made that the soot amount decreases as the speed of the engine 2 increases. Thus, the soot amount may be estimated with improved accuracy.

On the other hand, if the coolant temperature is equal to or lower than the low coolant temperature L in the high engine speed range where the speed of the engine 2 is relatively high (in particular, under a high load), the fuel injection period (i.e., the actual amount of time taken for fuel injection) increases, while the actual amount of time taken for the crank angle to change by one degree decreases. Then, the last stage of the injection period overlaps with a late phase of a compression stroke, and the fuel injected during the last stage of the injection time comes to adhere to the wall surface of the combustion chamber 28 more easily, thereby increasing the amount of soot formed. Therefore, if the coolant temperature is equal to or lower than the low coolant temperature L in the high engine speed range, estimation is made that the soot amount increases as the speed of the engine 2 increases. As a result, the soot amount may be estimated with improved accuracy.

If the temperature parameter is higher than the second temperature (i.e., the low coolant temperature L) and lower than the first temperature (i.e., the high coolant temperature H), the soot amount estimator 100 allows the rate of increase in the soot amount with the increase in the speed of the engine 2 to decrease in the high speed range as the temperature parameter increases (see the one-dot chain in FIG. 4).

As described above, if the coolant temperature is low, the fuel does not vaporize easily, and the higher the speed of the engine 2 is in the high speed range, the faster the gas flows in the combustion chamber 28, thus reducing the adhesion of the fuel to the wall surface of the combustion chamber 28. At the same time, however, the frequency of fuel injection per unit time increases, which increases the amount of soot formed in spite of the reduced adhesion of the fuel. On the other hand, once the coolant temperature is raised, the vaporization of the fuel is accelerated, and the amount of fuel left unvaporized in the combustion chamber 28 decreases accordingly, thereby reducing the soot formation. That is, in the high engine speed range, the rate of increase in the soot amount with the increase in the speed of the engine 2 decreases as the temperature parameter increases. Therefore, if the coolant temperature is higher than the low coolant temperature L and lower than the high coolant temperature H, the rate of increase in the soot amount with the increase in the speed of the engine 2 in the high engine speed range is allowed to decrease as the coolant temperature increases. Thus, the soot amount may be estimated with improved accuracy.

The soot amount estimator 100 stores first temperature data (i.e., the first temperature data map 101) representing the relationship among the speed of the engine 2, the load parameter, and the soot amount when the temperature parameter is the first temperature (i.e., the high coolant temperature H), and second temperature data (i.e., the second temperature data map 102) representing the relationship among the speed of the engine 2, the load parameter, and the soot amount when the temperature parameter is the second temperature (i.e., the low coolant temperature L). The soot amount estimator 100 estimates the soot amount ($h_{ij}$) based on the speed of the engine 2, the load parameter, and the first temperature data map 101 if the temperature parameter is equal to or higher than the first temperature, and estimates the soot amount ($1_{ij}$) based on the speed of the engine 2, the load parameter, and the second temperature data map 102 if the temperature parameter is equal to or lower than the second temperature. Further, if the temperature parameter is higher than the second temperature and lower than the first temperature, the soot amount estimator 100 calculates a first temperature soot amount ($h_{ij}$) based on the speed of the engine 2, the load parameter, and the first temperature data map 101, calculates a second temperature soot amount) based on the speed of the engine 2, the load parameter, and the second temperature data map 102, and estimates the soot amount by linear interpolation between the first and second temperature soot amounts.

According to this configuration, the soot amount may be estimated with improved accuracy while the amount of data stored in the soot amount estimator 100 is limited to the two data maps, namely, the first and second temperature data maps 101 and 102.

Although the two data maps consisting of the first and second temperature data maps 101 and 102 are used in the above-described configuration, three or more data maps may be used to estimate the soot amount.

Further, the soot amount estimator 100 may store the first temperature data map 101 only such that if the coolant temperature is lower than the high coolant temperature H, the soot amount may be estimated by multiplying the soot amount ($h_{ij}$) on the first temperature data map 101 by coefficients corresponding to the operational state and temperature of the engine.

What is claimed is:

1. A method for diagnosing degradation of a lubricant in an internal combustion engine, the method comprising:
   detecting a speed of the engine by a first sensor positioned to measure the speed of the engine and to output a speed detection signal;
   determining a load of the engine by a second sensor configured to detect a load parameter related to torque generated by the engine and configured to output a load detection signal;
   detecting a temperature parameter of the engine with a temperature sensor positioned on the engine, the temperature parameter being proportional to the temperature of a combustion chamber;
   estimating an amount of soot, formed in a predetermined period in the combustion chamber of the internal combustion engine, based on the detected speed of the internal combustion engine and the determined load related to torque generated by the internal combustion engine;
   calculating a cumulative value of the amount of soot estimated; and
   determining degradation of the lubricant in the internal combustion engine based on the cumulative value of the amount of soot;
   estimating the temperature of the combustion chamber based on the detected temperature, and correcting the amount of soot estimated into an increased value in response to when the estimated temperature of the combustion chamber is lower than a predetermined first temperature at which fuel injected into the combustion chamber vaporizes less with a decrease in temperature when estimating the amount of soot formed in the combustion chamber; and
   actuating an indicator when the corrected amount of estimated soot reaches a predetermined amount.

2. The method of claim 1, wherein
   when the detected temperature is equal to or lower than a predetermined second temperature that is lower than the predetermined first temperature,
   estimation is made that the amount of soot decreases as the detected speed of the internal combustion engine increases in a low engine speed range, and
   that the amount of soot increases as the detected speed of the internal combustion engine increases in a high engine speed range where the detected speed of the internal combustion engine is higher than in the low engine speed range.

3. The method of claim 2, wherein
   when the detected temperature is higher than the predetermined second temperature and lower than the predetermined first temperature, the rate of increase in the amount of soot with the increase in the detected speed of the internal combustion engine is allowed to decrease in the high engine speed range as the temperature parameter increases.

4. The method of claim 3, wherein
   the amount of soot is estimated based on the detected speed of the internal combustion engine, the determined load, and first temperature data when the temperature parameter is equal to or higher than the predetermined first temperature, and is estimated based on the detected speed of the internal combustion engine, the determined load, and second temperature data when the temperature parameter is equal to or lower than the predetermined second temperature,
   the first temperature data representing a relationship among the speed of the internal combustion engine, the determined load, and the amount of soot when the temperature parameter is the predetermined first temperature, and
   the second temperature data representing a relationship among the speed of the internal combustion engine, the determined load, and the amount of soot when the temperature parameter is the predetermined second temperature, and
   if the temperature parameter is higher than the predetermined second temperature and lower than the predetermined first temperature, a first temperature soot amount is calculated based on the detected speed of the internal combustion engine, the determined load, and the first temperature data, a second temperature soot amount is calculated based on the detected speed of the internal combustion engine, the determined load, and the second temperature data, and the amount of soot is estimated by linear interpolation between the first and second temperature soot amounts.

5. The method of claim 2, wherein
   the amount of soot is estimated based on the detected speed of the internal combustion engine, the determined load, and first temperature data when the detected temperature is equal to or higher than the predetermined first temperature, and is estimated based on the detected speed of the internal combustion engine, the determined load, and second temperature data when the detected temperature is equal to or lower than the predetermined second temperature,
   the first temperature data representing a relationship among the speed of the internal combustion engine, the load, and the amount of soot when the detected temperature is the predetermined first temperature, and
   the second temperature data representing a relationship among the speed of the internal combustion engine, the load, and the amount of soot when the detected temperature is the predetermined second temperature, and
   if the detected temperature is higher than the predetermined second temperature and lower than the predetermined first temperature, a first temperature soot amount is calculated based on the detected speed of the internal combustion engine, the determined load, and the first temperature data, a second temperature soot amount is calculated based on the detected speed of the internal combustion engine, the determined load, and the second temperature data, and the amount of soot is estimated by linear interpolation between the first and second temperature soot amounts.

6. An apparatus for diagnosing degradation of a lubricant in an internal combustion engine, the apparatus comprising:
a first sensor positioned to detect a speed of the internal combustion engine and to output a detection signal;
a second sensor configured to detect a load related to torque generated by the internal combustion engine and to output a detection signal;
a third sensor positioned to detect a temperature parameter being proportional to a temperature of a combustion chamber and to output a detection signal;
a soot amount estimator configured to receive the detection signals from the first, second, and third sensors, and to calculate an amount of soot formed in a predetermined period in the combustion chamber of the internal combustion engine based on the detected speed of the internal combustion engine and the load; and
a diagnostic unit configured to diagnose degradation of the lubricant based on a cumulative value of the amount of soot estimated by the soot amount estimator and to actuate an indicator when the amount of estimated soot reaches a predetermined amount, wherein
the soot amount estimator corrects, based on the temperature parameter, the amount of soot calculated into an increased value when estimating the temperature of the combustion chamber and determining the temperature of the combustion chamber to be lower than a predetermined first temperature, and the diagnostic unit actuates the indicator when the amount of estimated soot corrected by the soot amount estimator reaches the predetermined amount.

7. The apparatus of claim 6, wherein
when determining the temperature parameter to be equal to or lower than a predetermined second temperature that is lower than the predetermined first temperature and at which fuel injected into the combustion chamber vaporizes less with a decrease in temperature,
the soot amount estimator estimates that the amount of soot decreases as the detected speed of the internal combustion engine increases in a low engine speed range, and that the amount of soot increases as the detected speed of the internal combustion engine increases in a high engine speed range where the detected speed of the internal combustion engine is higher than in the low engine speed range.

8. The apparatus of claim 7, wherein
when determining the temperature parameter to be higher than the predetermined second temperature and lower than the predetermined first temperature, the soot amount estimator allows the rate of increase in the amount of soot with the increase in the detected speed of the internal combustion engine to decrease in the high engine speed range as the temperature parameter increases.

9. The apparatus of claim 8, wherein
the soot amount estimator stores
first temperature data representing a relationship among the detected speed of the internal combustion engine, the load, and the amount of soot when the temperature parameter is the predetermined first temperature, and
second temperature data representing a relationship among the detected speed of the internal combustion engine, the load, and the amount of soot when the temperature parameter is the predetermined second temperature, and
the soot amount estimator estimates the amount of soot based on the detected speed of the internal combustion engine, the load, and the first temperature data when determining the temperature parameter to be equal to or higher than the predetermined first temperature, and estimates the amount of soot based on the detected speed of the internal combustion engine, the load, and the second temperature data when determining the temperature parameter to be equal to or lower than the predetermined second temperature, and
when determining the temperature parameter to be higher than the predetermined second temperature and lower than the predetermined first temperature, the soot amount estimator calculates a first temperature soot amount based on the detected speed of the internal combustion engine, the load, and the first temperature data, calculates a second temperature soot amount based on the detected speed of the internal combustion engine, the load, and the second temperature data, and estimates the amount of soot by linear interpolation between the first and second temperature soot amounts.

10. The apparatus of claim 7, wherein
the soot amount estimator stores
first temperature data representing a relationship among the speed of the internal combustion engine, the load, and the amount of soot when the temperature parameter is the predetermined first temperature, and
second temperature data representing a relationship among the speed of the internal combustion engine, the load, and the amount of soot when the temperature parameter is the predetermined second temperature, and
the soot amount estimator estimates the amount of soot based on the detected speed of the internal combustion engine, the load, and the first temperature data when determining the temperature parameter to be equal to or higher than the predetermined first temperature, and estimates the amount of soot based on the detected speed of the internal combustion engine, the load, and the second temperature data when determining the temperature parameter to be equal to or lower than the predetermined second temperature, and
when determining the temperature parameter to be higher than the predetermined second temperature and lower than the predetermined first temperature, the soot amount estimator calculates a first temperature soot amount based on the detected speed of the internal combustion engine, the load, and the first temperature data, calculates a second temperature soot amount based on the detected speed of the internal combustion engine, the load, and the second temperature data, and estimates the amount of soot by linear interpolation between the first and second temperature soot amounts.

11. The apparatus of claim 6, wherein
the third sensor detects a temperature of a coolant in the internal combustion engine, and
the soot amount estimator estimates the temperature of the combustion chamber based on the temperature of the coolant being proportional to the temperature of the combustion chamber.

* * * * *